United States Patent [19]

Lesher et al.

[11] 4,225,601

[45] Sep. 30, 1980

[54] 3-HYDROXY OR HYDROXYMETHYL-5-(4-PYRIDINYL)2(1H)-PYRIDINONES, USEFUL AS CARDIOTONIC AGENTS AND THEIR PREPARATION

[75] Inventors: George Y. Lesher; Chester J. Opalka, Jr., both of Schodack, N.Y.

[73] Assignee: Sterling Drug Inc., New York, N.Y.

[21] Appl. No.: 73,885

[22] Filed: Sep. 10, 1979

[51] Int. Cl.$^2$ .................... C07D 401/04; A61K 31/44
[52] U.S. Cl. ..................................... 424/263; 546/257; 546/258
[58] Field of Search ................. 546/257, 258; 424/263

[56] References Cited

U.S. PATENT DOCUMENTS

| | | | |
|---|---|---|---|
| 4,072,746 | 2/1978 | Lesher et al. | 546/258 |
| 4,107,315 | 8/1978 | Lesher et al. | 546/258 |
| 4,137,233 | 1/1979 | Lesher et al. | 546/258 |

*Primary Examiner*—Alan L. Rotman
*Assistant Examiner*—Robert T. Bond
*Attorney, Agent, or Firm*—R. K. Bair; B. W. Wyatt

[57] ABSTRACT

3-(Hydroxy or hydroxymethyl)-5-(4-pyridinyl)-2(1H)-pyridinone or pharmaceutically-acceptable acid-addition salt thereof is useful as a cardiotonic agent. 3-Hydroxy-5-(4-pyridinyl)-2(1H)-pyridinone is prepared by autoclaving a mixture of an alkali lower-alkoxide, loweralkanol and 3-halo-5-(4-pyridinyl)-2(1H)-pyridinone and acidifying the cooled reaction mixture. 3-Hydroxymethyl-5-(4-pyridinyl)-2(1H)-pyridinone is prepared by reacting 5-(4-pyridinyl)-2(1H)-pyridinone with excess formaldehyde at an acidic pH. Said 3-(hydroxy or hydroxymethyl)-5-(4-pyridinyl)-2(1H)-pyridinone or pharmaceutically-acceptable acid-addition salt thereof is disclosed as the active ingredient in cardiotonic compositions for increasing cardiac contractility and in the method for increasing cardiac contractility in a patient requiring such treatment.

9 Claims, No Drawings

3-HYDROXY OR HYDROXYMETHYL-5-(4-PYRIDINYL)2(1H)-PYRIDINONES, USEFUL AS CARDIOTONIC AGENTS AND THEIR PREPARATION

BACKGROUND OF THE INVENTION (a) Field of the invention

This invention relates to 3-substituted-5-(4-pyridinyl)-2(1H)-pyridinones, useful as cardiotonic agents, and to their preparation.

(b) Description of the Prior Art

Lesher and Opalka U.S. Pat. No. 4,072,746, issued Feb. 7, 1978, shows certain 3-(unsubstituted and substituted)-5-(pyridinyl)-2(1H)pyridinones to be useful as cardiotonic agents, the 3-substituent being, inter alia, amino, alkylamino, dialkylamino, acylamino and cyano. Also shown as intermediates are corresponding 3-substituted compounds where the 3-substituent is nitro, halo or carbamyl.

SUMMARY OF THE INVENTION

In a composition aspect, the invention resides in the compound, 3-(hydroxy or hydroxymethyl)-5-(4-pyridinyl)-2(1H)-pyridinone or salt thereof, useful as a cardiotonic agent.

In a process aspect the invention comprises autoclaving a mixture of an alkali metal alkoxide, alkanol and 3-halo-5-(4-pyridinyl)-2(1H)-pyridinone and acidifying the reaction mixture to produce 3-hydroxy-5-(4-pyridinyl)-2(1H)-pyridinone.

In another process aspect the invention comprises reacting 5-(4-pyridinyl)-2(1H)-pyridinone with excess formaldehyde at an acidic pH to produce 3-hydroxymethyl-5-(4-pyridinyl)-2(1-H)-pyridione.

Another composition aspect of the invention relates to a cardiotonic composition for increasing cardiac contractility, said composition comprising a pharmaceutically-acceptable carrier and, as the active ingredient thereof, the cardiotonic 3-(hydroxy or hydroxymethyl)-5-(4-pyridinyl)-2(1H)-pyridinone or salt thereof.

In a method aspect, the invention relates to a method for increasing cardiac contractility in a patient requiring such treatment which comprises the administration of a medicament comprising a pharmaceutically-acceptable carrier and, as the active component thereof, the cardiotonic 3-(hydroxy or hydroxymethyl)-5-(4-pyridinyl)-2(1H)-pyridinone or salt thereof.

DETAILED DESCRIPTION INCLUSIVE OF PREFERRED EMBODIMENTS

In a composition aspect the invention resides in 3-(hydroxy or hydroxymethyl)-5-(4-pyridinyl)-2(1H)-pyridinone or pharmaceutically-acceptable acid-addition salt thereof. These compounds are useful as cardiotonic agents, as determined by standard pharmacological evaluation procedures.

A process aspect of the invention resides in the process which comprises heating under pressure a mixture of an alkali metal lower-alkoxide, lower-alkanol and 3-halo-5-(4-pyridinyl)-2-(1H)-pyridinone, and acidifying the reaction mixture to produce 3-hydroxy-5-(4-pyridinyl)-2(1H)-pyridinone. Sodium methoxide, methanol and 3-bromo-5-(4-pyridinyl)-2-(1H)-pyridinone are preferably used in this process. The word "lower" as used herein means "alkoxides" and "alkanols" each having from one to three carbon atoms.

In another process aspect the invention resides in the process of producing 3-hydroxymethyl-(4-pyridinyl)-2(1H)-pyridinone which comprises reacting 5-(4-pyridinyl)-2(1H)-pyridinone with excess formaldehyde at an acidic pH.

Another composition aspect of the invention resides in the cardiotonic composition for increasing cardiac contractility, said composition comprising a pharmaceutically-acceptable carrier and, as the active component thereof, the cardiotonic 3-(hydroxy or hydroxymethyl)-5-(4-pyridinyl)-2(1H)-pyridinone or pharmaceutically-acceptable acid-addition salt thereof.

A method aspect of the invention resides in the method for increasing cardiac contractility in a patient requiring such treatment which comprises administering to such patient an effective amount of the cardiotonic 3-(hydroxy or hydroxymethyl)-5-(4-pyridinyl)-2(1H)-pyridinone or pharmaceutically-acceptable acid-addition salt thereof.

The 3-(hydroxy or hydroxymethyl)-5-(4-pyridinyl)-2(1H)-pyridinone is useful both in the free base form and in the form of acid-addition salts, and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial cardiotonic properties inherent in the free base are not vitiated by side effects ascribable to the anions. In practicing the invention, it is convenient to form the free base form; however, appropriate pharmaceutically-acceptable salts within the scope of the invention are those derived from mineral acids such as hydrochloric acid, sulfuric acid, phosphoric acid and sulfamic acid; and organic acid such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid-addition salts of said basic compound are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said basic compound are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically-acceptable salt by ion exchange procedures.

The molecular structure of 3-(hydroxy or hydroxymethyl)-6-(4-pyridinyl)-2(1H)-pyridinone was assigned on the basis of evidence provided by infrared, nuclear magnetic resonance and mass spectra, by chromatographic mobilities, and, by the correspondence of calculated and found values for the elementary analyses.

The manner of making and using the instant invention will now be generally described so as to enable a person skilled in the art of pharmaceutical chemistry to make and use the same, as follows.

The reaction of 3-halo-5-(4-pyridinyl)-2(1H)-pyridinone with an alkali metal lower-alkoxide, loweralkanol to produce 3-hydroxy-5-(4-pyridinyl)-2(1H)-pyridinone is carried out by autoclaving the reactants, preferably using sodium methoxide, methanol and 3-bromo-5-(4-pyridinyl)-2(1H)-pyridinone at about 200° C., and acidifying the reaction mixture, preferably cooled.

The reaction of 5-(4-pyridinyl)-2(1H)-pyridinone with excess formaldehyde at an acidic pH to produce 3-hydroxymethyl-5-(4-pyridinyl)-2(1H)-pyridinone is carried out by heating the reactants at about 75° to 125° C. It is preferably run using an acidic pH of about 2.0 to 5.0, a large molar excess of formaldehyde and a reaction temperature of about 90° to 110° C. The quantity of formaldehyde can vary widely provided it is in excess of said 5-(4-pyridinyl)-2(1H)-pyridinone. In practice, a large excess, e.g., from about 10-fold to 100-fold or greater can be used; however, as little as a 2-fold excess or less of formaldehyde can be used although the reaction time is longer. Because of its ready availability and low cost, 37% aqueous formaldehyde solution is preferred.

The intermediates, 3-halo-5-(4-pyridinyl)-2(1H)-pyridinone and 5-(4-pyridinyl)-2(1H)-pyridinone, are shown, as are their preparations, in said Lesher and Opalka U.S. Pat. No. 4,072,746.

The following examples will further illustrate the invention without, however, limiting it thereto.

EXAMPLE 1

3-Hydroxy-5-(4-pyridinyl)-2(1H)-pyridinone, alternatively named 5-hydroxy-[3,4'-bipyridin]-6(1H)-one- A mixture containing 50 g. of 3-bromo-5-(4-pyridinyl)-2(1H)-pyridinone, 60 g. of sodium methoxide and 650 ml. of methanol was autoclaved at about 200° C. for twelve hours. The solvent was distilled off in vacuo and the residue was treated with water. The aqueous mixture was neutralized with acetic acid and the resulting solid was collected, washed with water and dried. The solid was recrystallized from dimethylformamide, washed successively with methanol and ether and dried to yield 11 g. of 3-hydroxy5-(4-pyridinyl)-2(1H)-pyridinone, m.p. >300° C.

Acod-addition salts of 3-hydroxy-5-(4-pyridinyl)-2(1H)-pyridinone are conveniently prepared by carefully adding to a mixture of 1 g. of 3-hydroxy-5-(4-pyridinyl)-1(1H)-pyridinone in about 20 ml. of aqueous methanol the appropriate acid, e.g., methanesulfonic acid, concentrated sulfuric acid, concentrated phosphoric acid, to a pH of about 2 to 3, chilling the mixture after partially evaporating and collecting the precipitated salt, e.g., dimethanesulfonate, sulfate, phosphate, respectively. Also, the acid-addition salt is conveniently prepared in aqueous solution by adding to water with stirring molar equivalent quantities each of 3-hydroxy-5-(4-pyridinyl)-2(1H)-pyridinone and the appropriate acid, e.g., lactic acid or hydrochloric acid to prepare respectively the monolactate or monohydrochloride salt in aqueous solution.

EXAMPLE 2

3-Hydroxymethyl-5-(4-pyridinyl)-2(1H)-pyridinone, alternatively named 5-(hydroxymethyl)-[3,4'-bipyridin]-6(1H)-one- A mixture containing 17.2 g. of 5-(4-pyridinyl)-2(1H)-pyridinone, 100 ml. of 37% formaldehyde and 300 ml. of 15% aqueous sulfuric acid was heated on a steam bath for about 20 hours. A tlc analysis of a sample of the reaction mixture using 3:1 v/v ethyl acetate/methanol indicated that starting material was still present. An additional 100 ml. of formaldehyde was added and the mixture heated for an additional 8 hours and then allowed to cool to room temperature. When starting material was still found to be present by tlc analysis as above, an additional 200 ml. of formaldehyde was added and the mixture heated for an additional 32 hours. The reaction mixture, which then contained no starting material, was cooled, neutralized with ammonium hydroxide and cooled again. The resulting precipitate was collected, washed with water and dried. The solid was recrystallized from about 600 ml. of water and dried to yield 12 g. of 3-hydroxymethyl-5-(4-pyridinyl)-2(1H)-pyridinone, m.p. 219°–220° C. with decomposition.

Acid-addition salts of 3-hydroxymethyl-5-(4-pyridinyl)-2(1H)-pyridinone are conveniently prepared by carefully adding to a mixture of 1 g. of 3-hydroxymethyl-5-(4-pyridinyl)-2(1H)-pyridinone in about 20 ml. of aqueous methanol the appropriate acid, e.g., methanesulfonic acid, concentrated sulfuric acid, concentrated phosphoric acid, to a pH of about 2 to 3, chilling the mixture after partially evaporating and collecting the precipitated salt, e.g., dimenthanesulfonate, sulfate, phosphate, respectively. Also, the acid-addition salt is conveniently prepared in aqueous solution by adding to water with stirring molar equivalent quantitites each of 3-hydroxymethyl-5-(4-pyridinyl)-2(1H)-pyridinone and the appropriate acid, e.g., hydrochloric acid or lactic acid to prepare respectively the monohydrochloride or monolactate salt in aqueous solution.

The usefulness of 3-(hydroxy or hydroxymethyl)-5-(4-pyridinyl)-2(1H)-pyridinone or salt as cardiotonic agent is demonstrated by its effectiveness in standard pharmacological test procedures, for example, in causing a significant increase in the contractile force of the isolated cat atria and papillary muscle and in causing a significant increase in the cardiac contractile force in the anesthetized dog with low or minimal changes in heart rate and blood pressure. These test procedures are described in the following paragraphs.

Isolated Cat Atria and Papillary Muscle Procedure - Cats of both sexes, weighing 1.5 to 3.5 kg. are each anesthetized with 30 mg./kg. i.p. of sodium pentobarbital and exsanguinated. The chest of each cat is opened, the heart excised, rinsed with saline, and the two atria and one or more small, thin papillary muscles from the right ventricle are dissected. The tissues are then transferred to a Petri dish filled with cold modified Tyrode's solution and bubbled with $O_2$. A silver wire is attached to each of two opposite ends of the tissue and one of the wires is hooked to a glass electrode. The preparation is then immediately mounted in a 40 or 50 ml. organ bath filled with modified Tyrode's solution at 37° C. The second wire is attached to a force-displacement transducer and the tension is adjusted to obtain a maximum contractile force (papillary muscle 1.5±0.5 g., left atria 3.0±0.6 g. right atria 4.5±0.8 g.). The transducer is connected to a Grass polygraph and the force and rate of contraction is recorded continuously. The right atrium is beating spontaneously due to the presence of the sino-atrial node, while the left atrium and the papillary muscle are stimulated electrically at a rate of 2 beats/sec. by a suprathreshold rectangular pulse of 0.5 millisecond duration.

The modified Tyrode's solution bathing the preparation is of the following composition (in millimoles): NaCl 136.87, KCl 5.36, $NaH_2PO_4$ 0.41, $CaCl_2$ 1.8, $MgCl_2.6H_2O$ 1.05, $NaHCO_3$ 11.9, glucose 5.55 and EDTA 0.04. The solution is equilibrated with a gas mixture consisting of 95% $O_2$ and 5% $CO_2$ and the pH is adjusted to 7.4 with dilute solution of sodium bicarbonate.

The preparation is left to equilibrate for one hour before any test compound is administered, and the bathing fluid is changed 3 to 4 times during the equilibration time. The 3-(hydroxy or hydroxymethyl)-5-(4-pyridinyl)-2(1H)-pyridinone dissolved in a vehicle (e.g., Tyrode's solution or aqueous solution of acid-addition salt of said compound tested) or the vehicle alone is added to the tissue bath and the full response is recorded. The tissues are washed between doses until pre-drug control values of rate and force of contraction are obtained. Four to six doses are given to the same preparation over a period of 4 to 6 hours.

When tested by the above-described Isolated Cat Atria and Papillary Muscle Procedure, 3-(hydroxy or hydroxymethyl)-5-(4-pyridinyl)-2(1H)-pyridinone, when tested at doses of 30, 100 or 300 $\mu$g./ml., was found to cause significant increase, that is, greater than 25% in papillary muscle force and a significant increase, that is, greater than 25%, in right atrial force, while causing only a low precentage increase (about one-third or less than the percentage increase in right atrial or papillary muscle force) in right atrial rate.

Anesthetized Dog Procedure—Mongrel dogs of both sexes weighing 9-15 kg. are used in this procedure. The dogs are each anesthetized with 30 mg./kg. i.v. sodium pentobarbital. Supplemental doses of pentobarbital are administered whenever necessary. An intratracheal cannula is inserted and ventilation is carried out by means of a Harvard constant-volume, positive pressure pump using room air. The right femoral artery is cannulated and the cannula is attached to a Statham P23A pressure transducer for the measurement of arterial blood pressure. The right femoral vein is cannulated and used for intravenous administration of compounds to be tested. Pin electrodes are attached to the right forelimb, right hindlimb and left hindlimb, and lead II electrocardiogram is monitored.

A ventro-dorsal incision at the third inter-costal space is made, the heart is exposed and a Walton-Brodie strain gauge is sutured to the wall of the right ventricle for the measurement of cardiac contractile force, that is, cardiac contractility. Aortic and coronary blood flow are measured with a pulsed field electromagnetic flow probe (Carolina Medical Electronics) inserted around the blood vessel in question. Aortic blood flow is used as an approximate index of cardiac output and total peripheral resistence is calculated from aortic flow and mean arterial pressure. All the above parameters measured are recorded simultaneously on a multi-channel Grass polygraph.

The test compound is administered intravenously as a single bolus injection of 0.30 to 10 mg./kg.

When tested by the above-described Anesthetized Dog Procedure, 3-(hydroxy or hydroxymethyl)-5-(4-pyridinyl)-2(1H)-pyridinone, when administered intravenously as a single bolus injection of 3 or 10 mg./kg. caused a significant increase, that is, greater than 25%, in cardiac contractile force or cardiac contractility with only low or minimal changes (less than 25%) in heart rate and blood pressure.

The present invention includes within its scope a cardiotonic composition for increasing cardiac contractility, said composition comprising a pharmaceutically-acceptable carrier and, as the active component thereof, the cardiotonic 3-(hydroxy or hydroxymethyl)-5-(4-pyridinyl)-2(1H)-pyridinone or pharmaceutically-acceptable acid-addition salt thereof. The invention also includes within its scope the method for increasing cardiac contractility in a patient requiring such treatment which comprises administering to such patient an effective amount of said 3-(hydroxy or hydroxymethyl)-5-(4-pyridinyl)-2(1H)-pyridinone or pharmaceutically-acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearte, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavouring, perfuming and preserving agents. According to the invention, the compounds for oral administration also include capsules of absorbable material, such as gelatin, containing said active component with or without the addition or diluents or excipients.

Preparations according to the invention for parenteral administration include sterile aqueous, aqueous-organic and organic solutions, suspensions and emulsions. Examples of organic solvents or suspending media are propylene glycol, polyethylene glycol, vegetable oils such as olive oil and injectable organic esters such as ethyl oleate. These compositions may also contain adjuvants such as stabilising, preserving, wetting, emulsifying and dispersing agents.

They may be sterilized, for examply by filtration through a bacteria-retaining filter, by incorporation of sterilising agents in the compositions, by irradiation or by heating. They may also be manufactured in the form of sterile solid compositions which can be dissolved in sterile water or some other sterile injectable medium immediately before use.

The percentages of active component in the said composition and method for increasing cardiac contractility may be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:

1. 3-(Hydroxy or hydroxymethyl)-5-(4-pyridinyl)-2(1H)-pyridinone or pharmaceutically-acceptable acid-addition salt thereof.

2. 3-Hydroxy-5-(4-pyridinyl)-2(1H)pyridinone.

3. 3-Hydroxymethyl-5-(4-pyridinyl)-2(1H)-pyridinone.

4. A cardiotonic composition for increasing cardiac contractility, said composition comprising a pharmaceutically-acceptable inert carrier and, as the active component thereof, and effective amount of the cardiotonic 3-(hydroxy or hydroxymethyl)-5-(4-pyridinyl)-2(1H)-pyridinone or pharmaceutically-acceptable acid-addition salt thereof.

5. A composition according to claim 4 where the active component is 3-hydroxy-5-(4-pyridinyl)-2(1H)-pyridinone.

6. A composition according to claim 4 where the active component is 3-hydroxymethyl-5-(4-pyridinyl)-2-(1H)-pyridinone.

7. The method for increasing cardiac contractility in a patient requiring such treatment which comprises administering orally or parenterally in a solid or liquid dosage form to such patient an effective amount of the cardiotonic 3-(hydroxy or hydroxymethyl)-5-(4-pyridinyl)-2(1H)-pyridinone or pharmaceutically-acceptable acid-acceptable salt thereof.

8. The process which comprises autoclaving a mixture of 3-bromo-5-(4-pyridinyl)-2(1H)-pyridinone, an alkali metal lower-alkoxide and lower-alkanol and acidifying the reaction mixture to produce 3-hydroxy-5-(4-pyridinyl)-2(1H)-pyridinone.

9. The process which comprises reacting 5-(4-pyridinyl)-2(1H)-pyridinone with excess formaldehyde at an acidic pH to produce 3-hydroxymethyl-5-(4-pyridinyl)-2(1H)-pyridinone.

* * * * *